United States Patent [19]

Bünning

[11] Patent Number: 5,618,525

[45] Date of Patent: Apr. 8, 1997

[54] HAIR TREATMENT COMPOSITION

[75] Inventor: Einhard Bünning, Seeheim-Jugenheim, Germany

[73] Assignee: Goldwell GmbH, Germany

[21] Appl. No.: 503,974

[22] Filed: Jul. 19, 1995

[30] Foreign Application Priority Data

Jul. 28, 1994 [DE] Germany .................. 44 26 794.0

[51] Int. Cl.$^6$ .................................................. A61K 7/075
[52] U.S. Cl. ........................................ 424/70.122; 524/588
[58] Field of Search ...................... 424/70.12, 70.122; 524/588

[56] References Cited

U.S. PATENT DOCUMENTS

| | | | |
|---|---|---|---|
| 4,331,167 | 5/1982 | Wajaroff | 424/70.12 |
| 4,659,777 | 4/1987 | Riffle et al. | 525/100 |
| 5,194,251 | 3/1993 | Halloran et al. | 424/70.12 |
| 5,286,476 | 2/1994 | Nanba et al. | 424/47 |
| 5,346,642 | 9/1994 | Patel et al. | 424/70.12 |

FOREIGN PATENT DOCUMENTS 640643  3/1995  European Pat. Off. .

OTHER PUBLICATIONS

Derwent accession No. 95–092299/13 for European application No. 640,643 and Japanese application Nos. 93–198657 and 93–199361 Aug. 1993.

Derwent accession No. 95–220818/29 for Japanese application Nos. 93–198657 and 93–199361 Aug. 1993.

*Primary Examiner*—Robert E. Sellers
*Attorney, Agent, or Firm*—Dvorak and Traub

[57] ABSTRACT

The invention comprises compositions for hair treatment containing at least one quaternized aminoalkyl dimethyl polysiloxane/polyethyl oxazoline copolymer of the formula

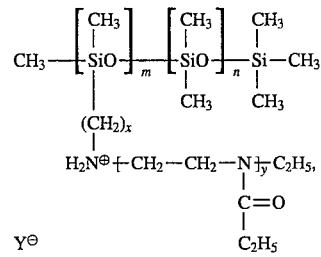

wherein m and n each denote integers from 20 to 10,000, x is a number between 1 and 5, and y is a number from 5 to 500, $Y^-$ being an anion, in at least one organic solvent. The composition is particularly useful for treating split hair ends.

3 Claims, No Drawings

HAIR TREATMENT COMPOSITION

This invention comprises a composition for hair treatment, especially for the treatment of split hair ends, having improved properties of use.

BACKGROUND OF THE INVENTION

1. Field of the Invention

Split hair ends are quite frequent symptoms for hair damage, particularly after stressing the hair by permanent waving, sun radiation, or thermal treatment, but also by mechanical or environmental influences.

A variety of compositions has already been suggested for the treatment of split hair ends or hair lengths, especially those basing on higher-grade viscous oils which, while inducing a certain adhesive effect, also produce an unattractive greasy appearance of the hair.

2. The Prior Art

European Patent Application 285,364 discloses compositions for treating split hair lengths or ends comprising a highly molecular silicone preferably in a solution with an oil or a silicone having a low-boiling point. To a certain degree, these compositions are also suitable for sealing split hair lengths or ends, however, due to their great hydrophobicity, they have the disadvantage that they cannot be rinsed out of the hair after treatment. Thus, these compositions provide the hair not only with an unesthetic look but also influence any optional subsequent hair treatments, particularly permanent-waving or hair dyeing.

Accordingly there was a need for hair treatment compositions which do not have these disadvantages.

SUMMARY OF THE INVENTION

This invention solves the problem by providing a composition for hair treatment which not only seals split hair ends but is also easily rinsed out of the hair, comprising a solution of at least one quaternized aminoalkyl, especially aminopropyl dimethyl polysiloxane/polyethyl oxazoline copolymer of the formula:

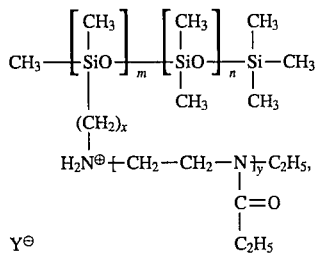

wherein m and n each denote integers from 20 to 10,000, particularly from 50 to 7,000, preferably from 100 to 5,000, x is a number between 1 and 5, preferably 3, and y is a number between 5 and 30, $Y^-$ is an anion; incorporated in at least one organic solvent.

Preferred organic solvents in this connection are lower alcohols, i.e. ethanol, n-propanol and isopropyl alcohol. The concentration of the grafted copolymer in the solution is preferably between about 10% to about 50%, particularly about 20% to about 40% by wt. calculated to the total composition.

The production of the aminoalkyl dimethyl polysiloxane/polyethyl oxazoline-grafted copolymers used in accordance with the invention is described in Japanese Patent Applications No. 05-198 657 of Aug. 10, 1993, and No. 05-199 361 of Aug. 11, 1993, complying with the following structure:

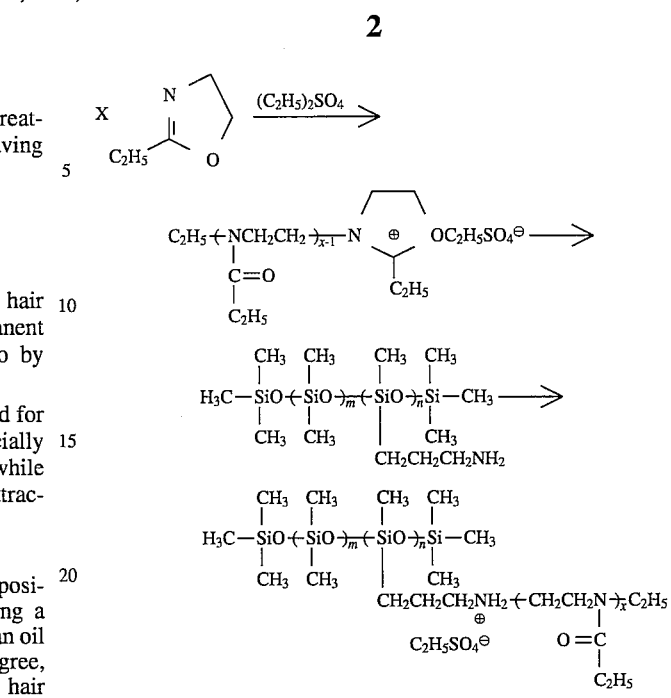

The anion $Y^\ominus$ of the general formula may naturally also be different from the ethyl sulfate anion of the above cited example, i.e. quaternization may also be effected with methyl chloride, dimethyl sulfate, benzyl chloride, dodecyl bromide, etc.

A particularly preferred grafted copolymer of the type described above has a total molecular weight from about 50,000 to about 150,000, preferably from about 80,000 to about 120,000, particularly about 100,000 Dalton, wherein the molecular weight of the oxazoline sequence is about 2,500 to about 7,500, preferably about 4,000 to about 6,000, particularly about 5,000 Dalton per sequence, i.e. the molecular proportion is about 20 units per molecule. The preferred silicone proportion is about 50% according to the elementary analysis.

Preferably, the compositions according to the invention comprise additionally at least one hydrocarbon with a boiling point between about 35° and about 280° C. (under normal pressure) and (or) at least one volatile silicone. Volatile silicones are particularly dimethicone, phenyl dimethicone and cyclomethicone of the general formulae

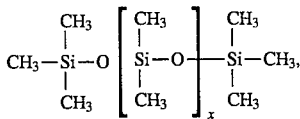

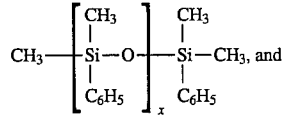

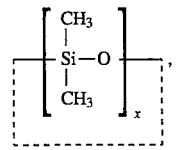

wherein x denotes low numbers between about 1 and about 10, in the event of the first mentioned dimethicone also between 0 and 10.

Preparations of this type are available on the market, e.g., under the trade names "Dow Corning® 200, 225, 244, 235, 344, 345 Fluid" or "SF-1202 or SF-1204 Silicone Fluid".

The viscosities of these volatile silicones are between about 0.5 and about 500 cSt at 25° C., particularly about 1 to about 100, preferably about 5 to about 50 cSt at 25° C.

Suitable hydrocarbons are hexane, isohexane, heptane, octane, nonane, decane, dodecane, tetradecane, hexadecane, octadecane and the isomers thereof as well as hydrocarbon mixtures, particularly preferred is isohexadecane.

The proportion of volatile silicones or hydrocarbons in the boiling range defined above is about 20% to 60% by wt., preferably 30% to 50% by wt. of the total composition.

The composition according to the invention is prepared as an organic solution which, if desired, may naturally also be packed as aerosol spray in a basically known process.

Other ingredients, such as perfumes, softening agents, and further natural and synthetic resins, etc., which are usual in hair care preparations, may also be added.

The following examples illustrate the invention in detail.

EXAMPLE 1

| Aminopropyl dimethyl polysiloxane/ polyethyl oxazoline-grafted copolymer | 30% (by wt.) |
|---|---|
| Isohexadecane | 40 |
| Ethanol | 30 |
| Perfume | q.s. |

This composition according to the invention was applied onto 10 strands with split hair ends in a comparison test. The solution was applied with thumb and forefinger from the hair roots to hair ends. After 5 minutes processing time the hair strands were washed and evaluated manually as well as visually under a stereo photo-microscope.

In a parallel assay 10 hair strands were treated correspondingly with a composition corresponding to the prior art, comprising

| Non-volatile dimethyl polysiloxane | (Viscosity: 50,000 cSt at 25° C.) | 20% by wt. |
|---|---|---|
| Volatile dimethyl polysiloxane | (Viscosity: 5 cSt at 25° C.) | 80% by wt. |

The evaluation showed that the hair ends treated with the composition according to the invention were completely sealed evenly and no product residues were left in the hair. The hair strands treated with the known composition showed an uneven tackiness at the ends; moreover, the preparation itself could not completely be rinsed out of the hair.

The following Examples 2 and 3 describe compositions which conform to a wide extent with the properties of the formula of Example 1.

EXAMPLE 2

| Aminopropyl dimethyl polysiloxane/polyethyl oxazoline-grafted copolymer | 25% (by wt.) |
|---|---|
| Cyclomethicone (Dow Corning ® 245 Fluid) | 30 |
| Ethanol | 45 |
| Perfume | q.s. |

EXAMPLE 3

| Aminopropyl dimethyl polysiloxane/ polyethyl oxazoline-grafted copolymer | 30 (% by wt.) |
|---|---|
| Dimethicone (Dow Corning ® 200 Fluid) | 40 |
| Ethanol | 30 |
| Perfume | q.s. |

I claim:

1. Hair treatment composition comprising a solution of at least one quaternized aminoalkyl dimethyl polysiloxane/polyethyl oxazoline copolymer of the formula

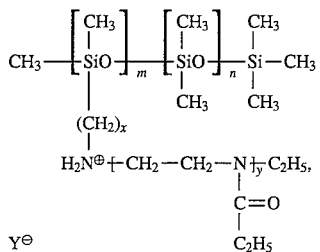

wherein m and n each denote integers from 20 to 10,000, x is a number between 1 and 5, and y is a number from 5 to 500, Y⊖ being an anion, in at least one organic solvent.

2. The composition according to claim 1, wherein the organic solvent is selected from the group consisting of ethanol, n-propanol and isopropyl alcohol.

3. The composition according to claim 1, further comprising a hydrocarbon having a boiling point between 35° C. and 280° C.

* * * * *